(12) United States Patent
Junginger et al.

(10) Patent No.: US 9,579,413 B2
(45) Date of Patent: Feb. 28, 2017

(54) HYDROGEL MATRIX HAVING IMPROVED ADHESIVE PROPERTIES

(75) Inventors: Martin Junginger, Hermaringen (DE); Julie Horny, Bollwiller (FR)

(73) Assignee: PAUL HARTMANN AG, Heidenheim (DE)

( * ) Notice: Subject to any disclaimer, the term of this patent is extended or adjusted under 35 U.S.C. 154(b) by 670 days.

(21) Appl. No.: 13/516,574

(22) PCT Filed: Dec. 14, 2010

(86) PCT No.: PCT/EP2010/007601
§ 371 (c)(1),
(2), (4) Date: Nov. 20, 2012

(87) PCT Pub. No.: WO2011/095194
PCT Pub. Date: Aug. 11, 2011

(65) Prior Publication Data
US 2013/0060216 A1 Mar. 7, 2013

(30) Foreign Application Priority Data
Dec. 24, 2009 (EP) .................................... 09016007

(51) Int. Cl.
*A61F 13/02* (2006.01)
*A61L 15/60* (2006.01)
*A61L 15/26* (2006.01)

(52) U.S. Cl.
CPC ............... *A61L 15/60* (2013.01); *A61L 15/26* (2013.01); *Y10T 156/10* (2015.01)

(58) Field of Classification Search
CPC .. A61F 2013/00225; A61F 2013/00229; A61F 2013/00548; A61F 2013/00421;
(Continued)

(56) References Cited

U.S. PATENT DOCUMENTS 3,978,855 A 9/1976 McRae et al.
4,393,048 A * 7/1983 Mason, Jr. .......... A61L 26/0023
424/619
(Continued)

FOREIGN PATENT DOCUMENTS

DE 10 2005 027656 A1 12/2006
DE 10 2006 016636 A1 10/2007
(Continued)

OTHER PUBLICATIONS

Contact Angle: retrieved from Internet: http://en.wikipedia.org/wiki/Contact_angle. Retrieved on Apr. 16, 2013.
(Continued)

*Primary Examiner* — Peter S Vasat
(74) *Attorney, Agent, or Firm* — Dilworth & Barrese, LLP.

(57) ABSTRACT

The invention relates to a multi-layered wound dressing, particularly for the moist wound treatment, comprising a first layer as a wound contact layer, which contains an aqueous hydrogel matrix, and at least a second absorbing layer. The hydrogel matrix comprises 37 to 43% by weight of propylene glycol, a prepolymer with isophorone diisocyanate groups and a diamine on the basis of polyethylene oxide in an amount of a total of 12 to 16.5% by weight, 0 to 5% by weight of an inorganic chloride, and the remainder water, wherein the ratio of the reactive groups of isocyanate to the amine groups of the diamine should be 1.25 to 1.35.

14 Claims, 2 Drawing Sheets

Figures 3, 3A:
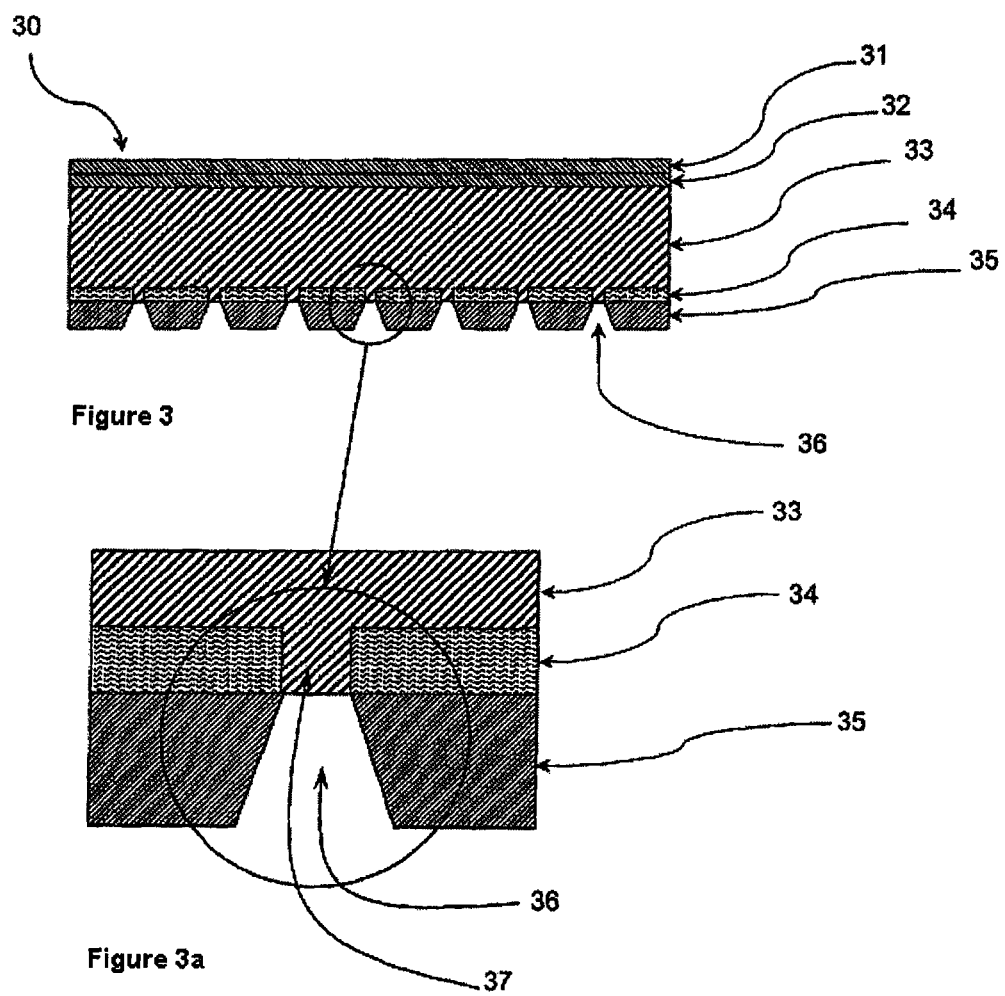

(58) Field of Classification Search
CPC .. A61F 2013/00561; A61F 2013/00604; A61F 2013/00608; A61F 2013/00655; A61F 2013/00676; A61F 2013/00748; A61F 2013/00757; A61F 2013/00761; A61F 13/0213; A61F 13/0246; A61F 13/0253; A61F 13/00987; A61F 2013/00782; A61L 15/16; A61L 15/18; A61L 15/22; A61L 15/225; A61L 15/24; A61L 15/26; A61L 15/60

See application file for complete search history.

(56) References Cited

U.S. PATENT DOCUMENTS

| | | | |
|---|---|---|---|
| 5,064,653 A * | 11/1991 | Sessions et al. | 424/445 |
| 5,106,629 A | 4/1992 | Cartmell et al. | |
| 5,292,777 A | 3/1994 | Desmarais et al. | |
| 5,429,589 A | 7/1995 | Cartmell et al. | |
| 5,489,262 A * | 2/1996 | Cartmell et al. | 602/57 |
| 5,569,207 A | 10/1996 | Gisselberg et al. | |
| 5,635,201 A * | 6/1997 | Fabo | 424/443 |
| 5,844,013 A | 12/1998 | Kenndoff et al. | |
| 6,034,149 A | 3/2000 | Bleys et al. | |
| 6,051,747 A * | 4/2000 | Lindqvist et al. | 602/46 |
| 6,977,323 B1 | 12/2005 | Swenson | |
| 7,943,811 B2 | 5/2011 | Da Silva Macedo, Jr. | |
| 8,147,857 B2 | 4/2012 | Fugmann et al. | |
| 2003/0120229 A1* | 6/2003 | de Jong et al. | 604/367 |
| 2004/0122388 A1* | 6/2004 | McCormack et al. | 604/360 |
| 2004/0123590 A1 | 7/2004 | Tabata et al. | |
| 2004/0153040 A1 | 8/2004 | Martineau et al. | |
| 2004/0241214 A1* | 12/2004 | Kirkwood | A61F 13/0213 424/445 |
| 2005/0123590 A1 | 6/2005 | Burton et al. | |
| 2005/0226917 A1 | 10/2005 | Burton | |
| 2006/0149017 A1* | 7/2006 | Graham | C08G 18/10 528/44 |
| 2006/0200063 A1 | 9/2006 | Munro et al. | |
| 2008/0255493 A1 | 10/2008 | Sigurjonsson et al. | |
| 2009/0214651 A1* | 8/2009 | Fugmann et al. | 424/486 |
| 2009/0216168 A1 | 8/2009 | Eckstein | |

FOREIGN PATENT DOCUMENTS

| | | |
|---|---|---|
| EP | 0426422 A2 | 5/1991 |
| EP | 0528091 A1 | 2/1993 |
| EP | 0630629 A2 | 11/1994 |
| EP | 0486522 B1 | 12/1994 |
| EP | 0457977 B1 | 2/1995 |
| EP | 0 455 324 B1 | 6/1995 |
| EP | 0455324 B1 | 6/1995 |
| EP | 0567704 B1 | 2/1997 |
| EP | 0693913 B1 | 3/1998 |
| EP | 0541391 B1 | 6/1998 |
| EP | 0541390 B1 | 7/1998 |
| EP | 0665856 B1 | 1/1999 |
| EP | 0691113 B | 7/2000 |
| EP | 0691113 B1 | 7/2000 |
| EP | 0570430 B1 | 1/2002 |
| EP | 0855921 B1 | 1/2002 |
| EP | 1007597 B1 | 4/2003 |
| EP | 1082146 B1 | 4/2005 |
| EP | 1156838 B1 | 5/2005 |
| EP | 1658865 A1 | 5/2005 |
| GB | 2428581 | 2/2007 |
| WO | 9213576 A1 | 8/1992 |
| WO | 9423678 A1 | 10/1994 |
| WO | 02/47761 A2 | 2/2002 |
| WO | 02/38097 A1 | 5/2002 |
| WO | 02/45761 A1 | 6/2002 |
| WO | 03/011352 A1 | 2/2003 |
| WO | 03/086255 A1 | 10/2003 |
| WO | 2003/092756 A1 | 11/2003 |
| WO | 2004/052415 A1 | 6/2004 |
| WO | 2007/113453 A1 | 10/2007 |
| WO | 2008/055586 A1 | 5/2008 |

OTHER PUBLICATIONS

Corresponding U.S. Appl. No. 13/000,845.

* cited by examiner

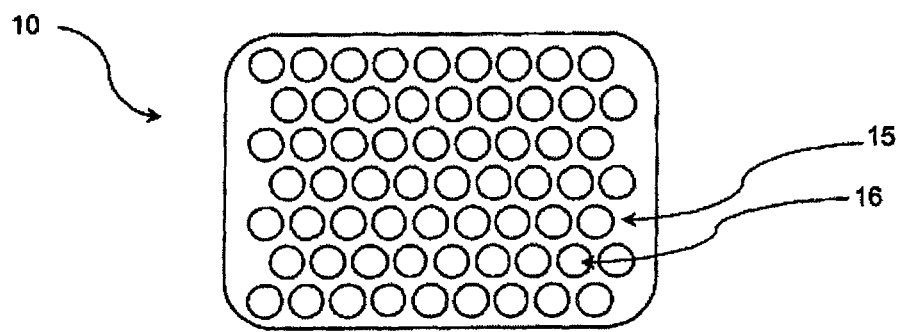
Figure 1
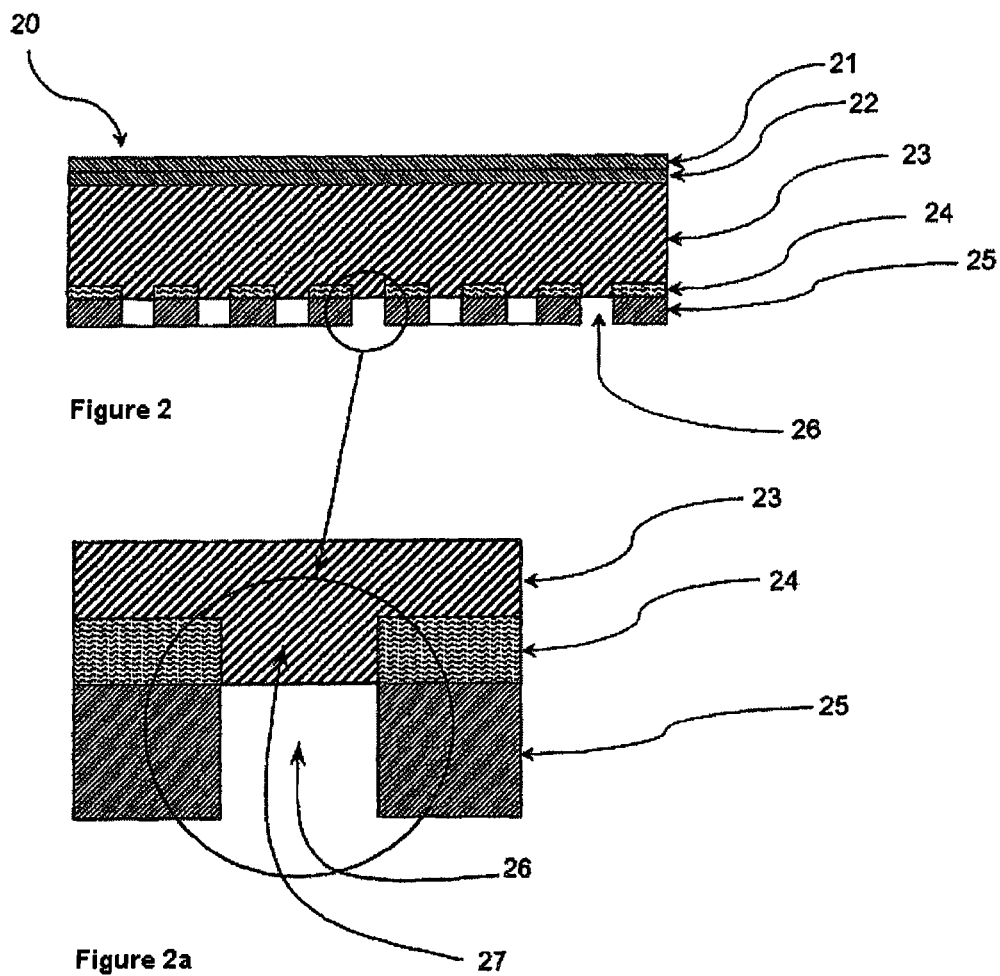
Figure 2
Figure 2a

HYDROGEL MATRIX HAVING IMPROVED ADHESIVE PROPERTIES

BACKGROUND OF THE INVENTION

This invention concerns wound dressings particularly as wound treatment means in the granulation and epithelization phase. These wound dressings are useful for moist treatment of wounds in particular.

The healing of skin wounds is based on the ability of the skin to regenerate epithelium and also connective and supporting tissue. Regeneration itself is characterized by a complex interplay of overlapping cellular activities which advance the healing process step by step. Three essential healing phases of a wound have been described in the literature irrespective of the type of wound. They include the inflammatory or exudative phase for blood coagulation and wound cleaning (phase 1, cleaning phase), the proliferative phase for building granulation tissue (phase 2, granulation phase) and the differentiation phase for epithelization and scar formation (phase 3, epithelization phase).

Numerous proposals for augmenting the individual wound healing phases are described in the literature. Especially wound dressings comprising hydrogels have for some time been the subject matter of numerous articles in the technical literature and also of patent documents. The European patents EP 455 324 B1, EP 528 091 B1, EP 567 704 B1 or EP 630 629 B1, for instance, describe transparent hydrogel wound dressings having various constructions. These sometimes multilayered wound dressings comprise a water-containing or dehydrated hydrogel as wound contact layer for the treatment of burn wounds.

EP0426422B1 discloses a wound dressing comprising a hydrogel based on a polyurea-polyurethane copolymer. The compositions described contain 15 to 30 wt % of a polyhydric alcohol. The ratio for reactive groups of isocyanate to amine groups in the hydrogel compositions described in EP0426422B1 is in the range from about 0.63 to 1.40. The ratio is 1.23 in an embodiment said to be preferred. A wound dressing which contains a hydrogel according to the compositions described in EP0426422B1 is on the market under the designation Hydrosorb® (Paul Hartmann AG, Germany). The wound dressing is capable of absorbing about twice its own weight of liquid within a period of 48 hours.

Furthermore, the European patents EP 457 977 B1, EP 486 522 B1, EP 541 390 B1, EP 541 391 B1, EP 570 430 B1, EP 665 856 B1, EP 691 113 B1, EP 693 913 B1 or EP 1 082 146 B1, for example, describe wound dressings having various constructions where the absorbent layer comprises a polyurethane foam.

In addition, the European patents EP 855 921 B1 and EP 1 156 838 B1 disclose wound dressings comprising a polyurethane foam coated with a hydrophobic silicone gel. This silicone gel is said to inhibit the adherence of the wound to the polyurethane foam.

Furthermore, the international applications WO 02/38 097 A1, WO 02/47 761 A1, WO 03/011 352 A1, WO 03/086 255 A1, WO 2004/052 415 A1 or EP 1 658 865 A1 describe wound dressings comprising a hydrogel and a polymer foam.

The applicant's application for patent under application number DE102008031183.9, which constitutes state of the art within the meaning of EPC Article 54(3) likewise describes a multilayered or multi-ply wound dressing having a wound contact layer as first layer and at least one second layer as absorbent layer which comprises a hydrophilic foam of polyurethane. The wound contact layer can be a hydrogel based on a polyurea-polyurethane copolymer. The operative example of DE102008031183.9 discloses a hydrogel comprising 17.5 wt % of propylene glycol, while the ratio for reactive groups of isocyanate to amine groups in the hydrogel described is 1.23. Using the polyurea-polyurethane copolymers described as wound contact layer in multilayered bandages provides atraumatic wound dressings having very good wound healing properties. A wound contact layer composed of the polyurea-polyurethane copolymers described is stable. However, a multilayered wound dressing incorporating a wound contact layer of this type has only minimal tack in respect of surrounding wound tissue. The wound dressing has to be held on the wound by hand until fixed in place by a bandage or an adhesive plaster.

State-of-the-art wound treatment requires wound dressings which speed the healing of wounds and augment the natural wound healing process. Suitable wound dressings have to combine different desirable properties. In addition to having very good skin and tissue compatibility, a wound dressing shall ensure the moist milieu which promotes wound healing, while excess liquid should be absorbed. A wound dressing shall further have atraumatic properties, i.e., the wound dressing must be removable when it needs to be changed, without damaging newly grown wound tissue. The wound contact layer here plays an outstanding part not only in respect of the desired atraumatic property but also for providing a milieu beneficial to wound healing, owing to its direct contact with the wound tissue. A moist milieu is beneficial for wound healing, although an alkaline pH, especially above pH 8, should be avoided. At the same time, excess liquid shall be transported out of the wound region and be absorbed by the wound dressing. Excess liquid or exudate can otherwise lead to maceration of the edge of the wound. Users, such as physicians or care personnel, frequently also desire in practice that a wound dressing adhere to the wound site even before it is fixed in place by a bandage or an adhesive plaster, i.e., the wound dressing shall have a certain amount of surface tack. This is desirable particularly in the case of wound dressings that are fixed to the body using a further bandaging means, such as a retaining bandage or an adhesive plaster. If the wound dressing has tack, the person applying the treatment can initially secure the wound dressing loosely on the wound and thereafter for example ready a suitable retaining bandage without at the same time having to use a hand to press down the wound dressing on the wound. A wound dressing with tack is substantially easier to use, especially when the dressing is applied by only one person. On the other hand, excessive force of adherence can lead to reducing the atraumatic property of the wound dressing and furthermore, when the dressing has to be changed, cause damage to the intact skin surrounding the wound. Excessive tack can also be less desirable because the positioning of a wound dressing which adheres too strongly to the wound tissue and to the healthy skin surrounding the wound is very difficult to correct after the first contact with the wound.

SUMMARY

In view of the described and commercially available wound dressings having a wound contact layer composed of a polyurea-polyurethane copolymer hydrogel matrix, the present invention has for its object to provide an improved wound dressing. The present invention more particularly has for its object to provide an improved wound dressing useful for wound healing in the granulation and/or epithelization phase. It is a further object of the present invention to provide an atraumatic wound dressing which influences the pathological state of a wound such that a normal, natural wound healing process can occur. To this end, the wound dressing shall provide a sufficient amount of moisture to the wound and at the same time have a wound-compatible pH close to neutral. It is more particularly desirable for the wound dressing to be able to adhere to the wound site and to the intact skin surrounding the wound, so that the wound dressing does not have to be held in place on the wound site until a retaining bandage or an adhesive plaster is applied. It is likewise desirable in this connection that the wound dressing have good absorptive capacity.

These objects are achieved by a multilayered wound dressing according to claim 1. A multilayered wound dressing according to the present invention accordingly comprises a first layer as a wound contact layer comprising a water-containing hydrogel matrix. The wound dressing further comprises at least one second absorbent layer. The hydrogel matrix comprises from 37 to 43 wt % of propylene glycol, altogether from 12 to 16.5 wt % of a prepolymer having isophorone diisocyanate end groups (hereinafter referred to as "isocyanate") and of a diamine based on polyethylene oxide and from 0 to 5 wt % of an inorganic chloride, balance water, wherein the ratio for reactive groups of isocyanate to amine groups of diamine shall be in the range from 1.25 to 1.35.

The proposed multilayered wound dressing rests on the surprising discovery that a hydrogel having improved tack is obtainable when the hydrogel comprises a composition which is characterized by a specifically selected amount of propylene glycol, of a prepolymer having isophorone diisocyanate end groups and of a diamine based on polyethylene oxide, provided there is a certain ratio for reactive groups of isocyanate to amine groups of diamine.

DETAILED DESCRIPTION OF THE INVENTION

A wound contact layer comprising a hydrogel matrix comprising from 37 to 43 wt % of propylene glycol, altogether from 12 to 16.5 wt % of a prepolymer having isophorone diisocyanate end groups and of a diamine based on polyethylene oxide and from 0.5 to 1.5 wt % of an inorganic chloride, balance water, wherein the ratio for reactive groups of isocyanate to amine groups of diamine is in the range from 1.25 to 1.35, adheres to the wound site, i.e., has sufficient tack. Tack with regard to the wound and the surrounding skin was assessed on a relative scale from 1 to 5 in the experimentation conducted in connection with the invention. It was assessed on the basis of the subjective impression of one person by comparison with the tack of various products as perceived between the index finger and the gel. Commercially available products were put into 5 categories by one person. A tack of 1 on the scale indicates that the wound dressing does not adhere to healthy skin, while a tack of 5 indicates a very high level of tack. A tack having the relative value of 4 is desirable in this context. The water-containing hydrogel wound contact layer disclosed in the present invention has sufficient tack, for example a tack with a value of 4, while the advantageous properties of the polyurea-polyurethane copolymer hydrogel matrix which are known from the prior art are retained or exceeded.

The combination comprising the water-containing hydrogel wound contact layer (first layer) and the absorbent layer (second layer) further has a very advantageous pH for wound healing close to neutral, for example about 7.3 to 7.5. The water-containing hydrogel is quick to cure and has suitable stability for use as wound contact layer in a multilayered wound dressing. Adequate stability on the part of the wound contact layer comprising the hydrogel is even ensured when the wound contact layer has holes, channels or openings occupying from 15 to 70% of the area of the wound contact layer.

To obtain the desired properties on the part of the water-containing hydrogel matrix, it is essential that the composition of the hydrogel matrix comprise firstly a propylene glycol content of 37 to 43 wt %. This is a significantly higher propylene glycol content compared with the compositions customarily described in the prior art. Secondly, the composition shall comprise altogether from 12 to 16.5 wt % of a prepolymer having isophorone diisocyanate end groups and of a diamine based on polyethylene oxide, subject to the proviso that the NCO:NH2 ratio for reactive groups of isocyanate ("NCO") to amine groups of diamine ("NH2") is adjusted to be in the range from 1.25 to 1.35. The hydrogel matrix further comprises from 0 to 5 wt % of at least one inorganic chloride. It was found that any departure from the composition disclosed in the invention provides a hydrogel having comparatively inferior properties, for example a hydrogel having a tack rated less than 3 or more than 4, a hydrogel having an undesirably high pH of more than 8 or a hydrogel that does not cure sufficiently.

Particularly advantageous hydrogels are obtainable when the composition comprises from 37 to 43 wt % of propylene glycol and preferably from 39 to 41 wt % of propylene glycol and altogether from 12 to 16.5 wt % and preferably from 14 to 16 wt % of a prepolymer having isophorone diisocyanate end groups and of a diamine based on polyethylene oxide, provided the ratio for reactive groups of isocyanate to amine groups of diamine is adjusted to be in the range from 1.27 to 1.33 and ideally in the range from 1.29 to 1.31. Hydrogels of this type have outstanding properties with regard to tack, pH and stability.

It will be found very advantageous for the hydrogel matrix to comprise from 0.5 to 1.5 wt % of an inorganic chloride, in which case the inorganic chloride is preferably sodium chloride. More particularly, the hydrogel matrix comprises 0.9 wt % of sodium chloride.

The hydrogel is obtainable by mixing water, propylene glycol and—if present—the inorganic chloride and then adding the molten amine under agitation until a homogeneous solution has formed. The isocyanate is then added. The gel is very quick to cure, typically within a few minutes, for example within 3 minutes. Curing, if desired, can be retarded by cooling the composition after the isocyanate has been added. The ratio for reactive groups of isocyanate to amine groups of diamine can be computed and adjusted in the usual manner from the molecular weights of the starting materials used having regard to their purity. For very accurate adjustment of the ratio for reactive groups of isocyanate to amine groups of diamine it is advantageous for the amine content of the mixture of water, propylene glycol, NaCl and diamine to be accurately measured in a manner known to a person skilled in the art before the isocyanate is added. The ratio for reactive groups of isocyanate to amine groups of diamine can be adjusted to a value in the range from 1.25 to 1.35, preferably in the range from 1.27 to 1.33 and ideally in the range from 1.29 to 1.31 via the amount of isocyanate added and having regard to the amine content measured. Particularly advantageous gels are obtained when the ratio for reactive groups of isocyanate to amine groups of diamine is adjusted to 1.30.

A particularly suitable wound contact layer for the multilayered wound dressing of the present invention comprises a hydrogel matrix having the following composition:
- 40 wt % of propylene glycol,
- 5.7 wt % of a diamine based on polyethylene oxide, for example Jeffamine ED-2003,
- 0.9 wt % of NaCl,
- 9.3 wt % of an isocyanate, for example Aquapol PI-13000-3,
- balance water.

The ratio for reactive groups of isocyanate to amine groups of diamine in the composition is 1.30.

A multilayered wound dressing which is in accordance with the present invention in comprising a hydrogel wound contact layer and an absorbent layer further has an unexpectedly high absorptive capacity for liquids. More particularly, a multilayered wound dressing which is in accordance with the present invention in comprising the hydrogel wound contact layer and a hydrophilic polyurethane foam having a water content of at least 10% has a particularly high absorptive capacity for liquids.

A wound dressing comprising a hydrogel 0.8 mm in thickness and a hydrophilic polyurethane foam 3 mm in thickness (water content about 58%) is capable of absorbing about 8.5 times its own weight of water within 48 hours. The hydrogel comprises 40 wt % of propylene glycol, 9.3 wt % of Aquapol isocyanate, 5.7 wt % of Jeffamine diamine based on polyethylene oxide, 0.9 wt % of NaCl and balance (about 44 wt %) water. The NCO:NH2 ratio for reactive groups of isocyanate to amine groups of diamine is 1.30. The aforementioned wound dressing displays a pH of 7.44, which is supportive of wound healing, and a tack of 4.

The at least one second layer of the multilayered wound dressing is an absorbent layer which preferably comprises a hydrophilic polyurethane foam, wherein the polyurethane foam comprises a water content of at least 10 wt % of water.

It is particularly preferable for this second layer to comprise a hydrophilic polyurethane foam comprising a water content of at least 10 wt % of water.

More particularly, the second layer of a wound dressing which is in accordance with the present invention comprises a hydrophilic polymer foam, more particularly a hydrophilic polyurethane foam comprising a water content of at least 20 wt % of water, especially at least 30 wt % and most preferably at least 35 wt % of water. It is further preferably provided here that the hydrophilic polymer foam, more particularly the hydrophilic polyurethane foam comprise a water content of at most 80 wt % of water, especially at most 70 wt % and most preferably at most 65 wt % of water. More particularly, this water content forms a homogeneous distribution in the polymer matrix or the polyurethane matrix of the foam. More particularly, the hydrophilic polymer foam comprises a water content of at least 10 wt % and at most 80 wt % of water, wherein the water more particularly forms a homogeneous distribution in the hydrophilic polymer foam, especially in the hydrophilic polyurethane foam.

Here and hereinbelow, every content of an ingredient is to be understood in connection with the present invention—unless otherwise stated—as being in weight percent (wt %) based on the weight of the component comprising the ingredient.

The amount of water in the respective component is verified in connection with the present invention on the basis of the DIN EN 14079 standard, wherein the amount of water is computed as follows:

$$W_w = \frac{W_g - W_t}{W_g} \cdot 100\% \quad (1)$$

where
- $W_w$=weight of water in % based on total weight of component
- $W_g$=weight of water-containing component
- $W_t$=weight of dry component Hence in connection with the present invention a hydrophilic polymer foam having a water content of at least 10 wt % or a hydrophilic polyurethane foam having a water content of at least 10 wt % is to be understood as being a polymer foam or polyurethane foam that comprises at least 10 wt % of water that can be released by the polymer foam or polyurethane foam. In contradistinction thereto, what is not meant is the proportion of water possibly used for forming for example in the polymerization of the starting materials of the polymer foam or polyurethane foam. This water is covalently bonded and is not available for wound treatment. Nor is meant any water used in the course of the production of the foam. This water is withdrawn from the polymer foam, after or during its formation, usually by drying, for example by drying in an oven, and thus is also not available for wound treatment. Hence a wound dressing which is in accordance with the present invention includes a polymer foam or a polyurethane foam that comprises a water content which distinctly exceeds any residual level of water due to the production process, after drying.

A wound dressing which is in accordance with the present invention further preferably comprises a hydrophilic polyurethane foam having a retention value R of at least 20%. Further preferably, the hydrophilic polyurethane foam has a retention value R of at least 30%, more particularly of at least 40%, more particularly of at least 40% and most preferably of at least 50%.

Independently, it may further be preferable for the wound dressing to include a hydrophilic polyurethane foam having a retention value R of at most 90%, more particularly of at most 80% and very particularly of at most 70%. This retention value R is determined as per a method described herein.

It is very particularly preferable for a wound dressing which is in accordance with the present invention to comprise a hydrophilic polyurethane foam comprising a water content of at least 10 wt % wherein the water content corresponds to the retention value R of the polyurethane foam.

It is thus possible to provide a wound dressing that, in comparison to known hydrogel wound dressings, possesses a higher absorptive capacity and simultaneously a high water content. The wound dressing can release this water in the treatment of wounds and simultaneously imbibe any wound exudate present. In comparison to known polymer foam wound dressings, a wound dressing can be provided that supplies the wound surface with sufficient moisture or water and simultaneously possesses a sufficient absorptive capacity. This removes from the wound surface any negatives for wound healing, and at the same time provides moisture and water in a sufficient amount. Owing to the lower absorptive capacity compared with dry polymer foams, which do not comprise releasable water and usually absorb a lot of wound exudate very quickly, resulting in a dry wound surface, this wound dressing is very suitable for use in the epithelization or granulation phase of wound healing.

More particularly, the multilayered wound dressing of the present invention achieves an advantage due to the combination of an absorbent hydrophilic polymer foam that keeps the wound moist with a hydrogel wound contact layer which has a pH, for example between 7.3 and 7.5, that does not impair wound healing.

The hydrophilic polymer foam used in connection with the present invention can be any hydrophilic polymer foam customary today in state of the art wound healing and imbibing a water fraction in its polymer scaffold and yet having sufficient absorbency. Hence in connection with the present invention a hydrophilic polymer foam is a polymer foam capable of absorbing and storing fluids and of releasing at least a portion of these fluids again. More particularly, the polymer foam used can be a hydrophilic polyurethane foam, a hydrophilic polyether foam, a hydrophilic polyurethane-polyether copolymer foam, a hydrophilic polyvinyl acetate foam, hydrophilic polyvinyl alcohol foam, a hydrophilic collagen foam, a hydrophilic chitosan foam or mixtures thereof. It is very particularly preferable for a hydrophilic polyurethane foam to be used as polymer foam.

The present invention requires the use of such polymer foams, more particularly polyurethane foams as have a high absorptive capacity. This absorptive capacity shall be present even though the polymer foam, more particularly the polyurethane foam, has imbibed in its polymer matrix or its polyurethane matrix a fraction of its own weight of water. In a further development of the invention, therefore, a wound dressing that is in accordance with the present invention comprises a hydrophilic polymer foam, more particularly a hydrophilic polyurethane foam comprising a water fraction of at least 10 wt % and at most 80 wt % of water and having a free absorbency $A_2$ of at least 10 g/g, more particularly at least 12 g/g and most preferably of at least 15 g/g, the free absorbency $A_2$ being determined as per DIN-EN 13726-1 (2002). The free absorbency $A_2$ here is the free absorbency of the water-containing polymer foam or of the water-containing polyurethane foam.

It is further preferable for a wound dressing that is in accordance with the present invention to comprise a hydrophilic polymer foam, more particularly a hydrophilic polyurethane foam comprising a water fraction of at least 10 wt % and at most 80 wt % of water and having a free absorbency $A_1$ of at least 10 g/g, more particularly at least 12 g/g and most preferably of at least 15 g/g, the free absorbency $A_1$ being determined as per DIN-EN 13726-1 (2002). The free absorbency $A_1$ here is the free absorbency of the dry polymer foam or of the dry polyurethane foam.

In a further development of the present invention, a wound dressing according to the present invention hence also comprises a second layer having a first and a second side as absorbent layer, wherein the second layer comprises the hydrophilic polymer foam or the hydrophilic polyurethane foam. More particularly, the first layer therein has direct contact to the second layer. However, it is also possible for the second layer as absorbent layer to have direct contact to a wound contact layer. A wound contact layer is in direct contact with the wound.

When the hydrophilic polymer foam used is a hydrophilic polyurethane foam, a wound dressing which, compared with wound dressings comprising dry hydrophilic polyurethane foams, exerts a very much smaller shearing stress on the wound can be provided. A water fraction of at least 10 wt % of water in the polymer foam makes it possible to provide a wound dressing having a preconditioned hydrophilic polyurethane foam and a very much smaller swell capacity with approximately equal absorption of liquids compared with a wound dressing having a dry hydrophilic polyurethane foam. The lower swell capacity of the preconditioned polyurethane foam thus ensures that, within the wound dressing, lower shearing forces prevail in respect of further plies or materials or in respect of a wound to be treated. This makes it possible to provide a polyurethane foam wound dressing that is particularly promotive in respect of wound healing.

Hence, in accordance with a further developed concept, the present invention also provides a wound dressing comprising a second ply having a first side and a second side, wherein the ply comprises a hydrophilic polyurethane foam comprising a water fraction of at least 10 wt % and having a swell capacity $\Delta V_1$ of at most 80%. More particularly, this hydrophilic polyurethane foam has a swell capacity $\Delta V_1$ of at most 60%, more particularly of at most 40%, more particularly of at most 30% and most preferably of at most 20%. It may further be advantageous in this connection for the polyurethane foam to have a residual swell capacity $\Delta V_1$ of at least 5%. This residual swell capacity can be utilized to achieve better contact between the wound dressing and the wound bed during absorption.

Swell capacity $\Delta V_1$ of a polyurethane foam is to be understood as meaning the increased volume of a polyurethane foam which has completely exhausted its absorptive capacity as compared with a polymer foam having a water content of at least 10 wt % of water. This swell capacity shall be determined as per a test described herein.

The polyurethane foam useful in connection with the present invention can be any hydrophilic polyurethane foam customary in state of the art wound treatment and absorbing a water fraction in its polyurethane matrix and having sufficient absorbency. Hence, in connection with the present invention, a hydrophilic polyurethane foam is a polyurethane foam that is capable of imbibing and storing, i.e., absorbing, a liquid in its polyurethane matrix and in its pores, and of rereleasing at least some of the imbibed liquid. Useful hydrophilic polymer foams include more particularly open-celled hydrophilic polyurethane foams. Accordingly, a particularly preferred wound dressing comprises a second layer comprising an open-celled hydrophilic polyurethane foam.

In a preferred embodiment of the invention, the wound dressing of the invention further comprises a hydrophilic polyurethane foam which in the dry state has an ISO1798-M1 elongation at break ranging from 50 to 105 kPa and preferably from 72 to 94 kPa. A hydrophilic polyurethane foam which in the dry state has an ISO1798-M1 elongation at break ranging from 50 to 72 and especially from 72 to 94 kPa is particularly suitable for the wound dressing of the present invention, since a wound dressing comprising such a polyurethane foam has sufficient stability and also is sufficiently conformable to the substrate.

It is further preferable for a wound dressing that is in accordance with the present invention to comprise a hydrophilic polymer foam, more particularly a hydrophilic polyurethane foam that has an average pore size of less than 1000 µm, more particularly in the range from 100 to 1000 µm, more particularly in the range from 100 to 500 µm and most preferably in the range from 100 to 300 µm. In connection with the multilayered wound dressing that is in accordance with the present invention, a hydrophilic polyurethane foam with a pre size of 150 to 220 µm will be found particularly advantageous, the pore size being determined microscopically. More particularly, the average pore size on the first side of the second layer may be equal to the pore size in the interior of the second layer and/or the same size as on the second side of the second layer. Further preferred hydrophilic polyurethane foams have a density of less than 150 kg/m$^3$, more particularly less than 140 kg/m$^3$ and most preferably in the range from 50 to 120 kg/m$^3$. Particularly advantageous embodiments further comprise wound dressings comprising a hydrophilic polymer foam, more particularly a polyurethane foam, having a layer thickness in the range from 0.1 to 10.0 mm. More particularly, therefore, a wound dressing that is in accordance with the present invention includes an absorbent layer having a layer thickness in the range from 0.1 to 6.0 mm, more particularly in the range from 0.5 to 6.0 mm and most preferably in the range from 2.0 to 5.5 mm. Wound dressings having such layer thicknesses are able to imbibe a wound's exudate and at the same time can provide a sufficient amount of water or moisture to a wound.

This advantageous effect is further amplified by a wound contact layer comprising a water-containing hydrogel matrix having a layer thickness in the range from 0.6 to 1.0 mm. In a preferred embodiment of the invention, the multilayered wound dressing comprises a) a first layer as a wound contact layer comprising a water-containing hydrogel matrix having a layer thickness of 0.8 mm, and b) a second absorbent layer which comprises a hydrophilic polyurethane foam having a layer thickness of 4.0 mm, wherein the first layer and the second layer are in direct contact with each other.

In a further very advantageous embodiment of the invention, the multilayered wound dressing comprises a) a first layer as a wound contact layer comprising a water-containing hydrogel matrix having a layer thickness of 0.8 mm, and b) a second absorbent layer which comprises a hydrophilic polyurethane foam having a layer thickness of 2.8 mm, wherein the first layer and the second layer are in direct contact with each other. These layer thicknesses can be the same at every point of the wound contact layer, or differ in various regions of the wound contact layer. It is more particularly provided that the absorbent layer or the polyurethane foam has flattened edges.

The present invention further provides that the wound dressing that is in accordance with the present invention comprises as wound contact layer a water-containing hydrogel matrix comprising at least 39.5 wt % and more particularly at least 43 wt % of water, in which case the hydrogel matrix further preferably comprises at most 50 wt % of water. It is thus possible to provide a wound dressing which provides moisture in an amount sufficient for natural wound healing.

Useful water-containing hydrogel matrices in connection with the present invention include in particular hydrogel matrices that form a coherent, discrete layer and do not release water under pressure. The hydrogel matrices in connection with the present invention are hydrogel matrices comprising a polyurethane-polyurea copolymer. These hydrogel matrices are particularly useful for storing water and delivering this water to a wound.

The water-containing hydrogel matrix shall further contain from 37 to 43 wt % of propylene glycol. This alcohol is outstandingly useful as moisture donor and thus constitutes a care component for the skin surrounding the wound.

In this connection, the water-containing hydrogel matrix shall comprise more particularly from 37 to 43 wt % of the polyhydric alcohol propylene glycol. More particularly, the hydrogel matrix comprises from 39 to 41 wt % of propylene glycol and most preferably 40 wt % of propylene glycol.

It is further an essential feature of the invention that the NCO:NH2 ratio for reactive groups of isocyanate (NCO) to amine groups of diamine (NH2) is in the range from 1.25 to 1.35, since it is only then that the advantageous tack of the hydrogel matrix is obtained without adversely affecting other properties, for example the pH or the stability of the hydrogel. More particularly, the ratio for reactive groups of isocyanate to amine groups of diamine shall be in the range from 1.27 to 1.33 and preferably in the range from 1.29 to 1.31. A ratio for reactive groups of isocyanate to amine groups of diamine in the region of 1.30 is particularly advantageous.

It is further envisioned that the water-containing hydrogel matrix comprises at least one inorganic chloride. Sodium chloride, potassium chloride, magnesium chloride, calcium chloride or mixtures thereof are particularly suitable in this connection. These salts are particularly good at simulating the electrolyte mixture in wound serum. As a result, a hydrogel matrix comprising these salts provides similar osmotic conditions between hydrogel and wound exudate and thereby a wound with a climate that is particularly promotive of wound healing.

One possibility here is for the hydrogel matrix to comprise from 0 to 5 wt % of at least one inorganic chloride. More particularly, the hydrogel matrix comprises from 0.1 to 3 wt % of an inorganic chloride and most preferably from 0.5 to 1.5 wt % of an inorganic chloride. A hydrogel matrix containing 0.9 wt % of sodium chloride will prove very advantageous.

A water-containing hydrogel matrix comprising from 37 to 43 wt % of propylene glycol, altogether from 12 to 16.5 wt % of a prepolymer having isophorone diisocyanate end groups and of a diamine based on polyethylene oxide and from 0.5 to 1.5 wt % of an inorganic chloride, balance water, wherein the ratio for reactive groups of isocyanate to amine groups of diamine shall be in the range from 1.25 to 1.35, has a free absorbency $A_3$ (measured to DIN EN 13726-1 (2002)) of at least 1 g/g and at most 10 g/g. The water-containing hydrogel matrix provides a nonirritant, liquid-absorbing, cushioning, skinlike medium that affords protection from bacteria, and thus is particularly useful as a wound contact layer.

According to the present invention, the first layer is a wound contact layer. A wound contact layer herein is a layer which can be in direct contact with the wound. The wound contact layer can have the sole purpose in the present invention of spacing the polyurethane foam away from the wound to be treated. The wound contact layer can also perform further functions in relation to the wound dressing as well as in relation to the wound to be treated. More particularly, a wound dressing that is in accordance with the present invention may comprise a wound contact layer which in addition to the hydrogel matrix further comprises a polymer film, a hydrocolloid matrix, a polymer mesh, a nonwoven or an adhesive.

Particularly advantageous embodiments further comprise wound dressings comprising a hydrogel matrix having a layer thickness in the range from 0.1 to 5.0 mm. More particularly, therefore, a wound dressing that is in accordance with the present invention includes a hydrogel matrix having a layer thickness in the range from 0.1 to 5.0 mm, more particularly in the range from 0.5 to 5.0 mm and most preferably in the range from 0.5 to 3.0 mm. Wound dressings having such layer thicknesses as a wound contact layer do not stick to wounds on the one hand and on the other hand are able to imbibe a wound's exudate and convey it onto an absorbent layer. A wound contact layer that is particularly suitable with regard to its cooperation with the second absorbent layer comprises a hydrogel matrix having a layer thickness of 0.6 to 1.0 mm, especially 0.8 mm. These layer thicknesses can be the same at every point of the wound contact layer, or differ in various regions of the wound contact layer.

It is further preferable for the hydrogel matrix to comprise channels, more particularly conical channels, to allow liquids to pass through from the first to the second side. This provides for improved passage of wound exudate in particular. It is particularly preferable for the channels to have an elliptical or circular cross section, i.e., for the channels to have a circular or elliptical opening both on the first side and on the second side of the hydrogel matrix and for the circular or elliptical opening on the first and second sides to differ in size. However, the channels may also have a triangular, rectangular, square, pentagonal, hexagonal or some other polygonal cross section. It is very particularly preferable for the first side to have openings larger than the openings on the second side.

In a further development of the invention, the hydrogel matrix may also have openings from 0.5 to 10 mm in diameter. More particularly, the wound contact layer or the hydrogel matrix has openings from 1 to 8 mm in diameter. It is very particularly preferable for the wound contact layer or the hydrogel matrix to have openings on the wound-facing first side which are from to 6 mm in diameter, while the second side of the wound contact layer or of the hydrogel matrix is in direct contact with the polyurethane foam.

A transition layer may also be disposed between the first layer and the second layer, more particularly between the first layer as wound contact layer and the second layer as absorbent layer. In this embodiment, a wound dressing that is in accordance with the present invention includes, between the hydrogel matrix and the polymer foam, more particularly between the hydrogel matrix and the polyurethane foam, a layer which comprises both the materials. This transition layer may have channels, openings or holes, just like the wound contact layer. When the transition layer has channels, openings or holes, it is a further preferred embodiment that these channels, openings or holes are filled with polyurethane foam. It is further preferable for these channels, openings or holes to be congruent to the channels, openings or holes in the wound contact layer. Providing such a transition layer makes it possible to provide a wound dressing comprising a laminate formed from a polyurethane foam and a hydrogel matrix and having a particularly firm bond between the absorbent layer and the wound contact layer.

The wound contact layer according to the present invention may utilize any material that has no adverse effect on wound healing. This wound contact layer can have the sole purpose of spacing the polyurethane foam or the hydrogel matrix away from the wound to be treated, but this wound contact layer can also perform further functions in relation to the wound dressing as well as in relation to the wound to be treated. More particularly, a wound dressing that is in accordance with the present invention may comprise a wound contact layer having a first side and a second side, in which case the wound contact layer comprises a hydrogel matrix.

In a further development of the wound dressing of the present invention, the wound contact layer may comprise a multiplicity of channels, openings or holes to let liquids pass through. A more particular provision in this connection is for the wound contact layer to include channels which form a passageway for wound exudate from the first side to the second side. In this embodiment, the first side of the wound contact layer is in direct contact with a wound to be treated and the second side of the wound contact layer is in direct contact with the first side of the absorbent layer.

More particularly, the wound contact layer may also have channels, openings or holes from 0.5 to 10 mm in diameter. More particularly, the wound contact layer includes channels, openings or holes from 3 to 6 mm in diameter. It is very particularly preferable for the wound contact layer to have on its first side (the side which faces the wound when the wound dressing is used as intended) openings from 4 to 5 mm in diameter, while the second side of the wound contact layer is in direct contact with the polyurethane foam. Here and hereinbelow the diameter of the channels, openings or holes relates to the middle diameter when the channels, openings or holes are conically styled channels, openings or holes. The middle diameter in this context is a diameter which is present in the middle of the particular layer, for example the wound contact layer. This middle diameter can be smaller in the case of conically shaped channels, openings or holes than the diameter of the channels, openings or holes on the first side and at the same time greater than the diameter of channels, openings or holes on the second side. Similarly, a separation of channels, openings or holes is to be understood as meaning the middle separation of the channels, openings or holes. Correspondingly, the separation between the rows is to be understood as meaning the middle separation between the rows.

It may further be preferable for the wound contact layer to have a multiplicity of channels, openings or holes to allow liquids to pass through, which channels, openings or holes on the first side of the wound contact layer occupy an area of at most 70% of the area of the first side of the wound contact layer. It is further preferable in this connection for the channels, openings or holes to occupy an area of at most 70%, more particularly at most 60% and most preferably of at most 50% of the area of the first side of the wound contact layer. It is very particularly preferable for the wound contact layer to have channels, openings or holes which on the first side of the layer occupy an area of at least 15% of the area of the first side of the wound contact layer. It is very particularly preferable for the wound contact layer to further have channels, openings or holes which on the first side of the layer occupy an area of at least 40% and at most 47% of the area of the first side of the wound contact layer. The wound dressing very particularly has.

The arrangement of channels, openings or holes can be embodied in offset rows in a very advantageous embodiment. A middle diameter of 4.5 mm for the channels, openings or holes will be found particularly advantageous. The separation of the midpoints of the channels, openings or holes in any one row is 6.5 mm, resulting in the formation of a gel strut between the channels, openings or holes which is 2 mm in width. The separation between the rows at 5.63 mm is chosen so as to form an equilateral triangle between the midpoints of three holes. This provides a homogeneous distribution of the open area of 43.5% across the product face. When the diameter of the holes is significantly smaller, thick exudate in particular is less capable of passing efficiently through the gel layer. Significantly larger holes, by contrast, lead either to a smaller gel area or to very broad struts which in turn can back up the wound exudate at this point. A smaller gel area has the effect that the overall product has less area from which to adhere and can thus reduce tack.

In accordance with another further developed concept of the present invention, the present invention also provides a wound dressing which includes a barrier layer between the hydrogel matrix and the hydrophilic polymer foam. Such a barrier layer may comprise for example a polymer film with openings.

A wound dressing that is in accordance with the present invention may further comprise a backing layer. This backing layer can consist of various materials. Typically, wound dressings utilize textile backing materials, nonwovens, polymer films or polymer foams. This backing layer may be in direct or indirect contact with the second side of the absorbent layer or with the hydrophilic polymer foam. In the case of direct contact, the backing layer is laminated directly onto the absorbent ply or the polyurethane foam, whereas in the case of indirect contact the backing layer is applied to the absorbent layer or the polyurethane foam by means of an adhesive. This adhesive may be applied between the backing layer and the absorbent layer in a uniform manner or merely in sub-regions.

The backing layer of a wound dressing that is in accordance with the present invention may utilize in particular polymer films or polymer foams. Very particular preference is given to polymer films or polymer foams which are water impermeable and have a high moisture vapor permeability. Films or foams particularly suitable for this are fabricated from polyurethane, polyether urethane, polyester urethane, polyether-polyamide copolymers, polyacrylate or polymethacrylate. More particularly, a water impermeable and moisture vapor permeable polyurethane film or a water impermeable and moisture vapor permeable polyurethane foam is suitable for use as backing layer. More particularly, a polyurethane film, polyester urethane film or polyether urethane film is preferable for use as polymer film. However, very particular preference is also given to polymer films from 15 to 50 µm, more particularly from 20 to 40 µm and most preferably from 25 to 30 µm in thickness. The moisture vapor transmission rate of the polymer film of the wound dressing is preferably at least 750 g/m$^2$/24 h, more particularly at least 1000 g/m$^2$/24 h and most preferably at least 2000 g/m$^2$/24 h (measured to DIN EN 13726). In particularly preferred embodiments, these films have a moisture-proof tacky edge portion. This edge portion ensures that the wound dressing can be applied to and fixed at its intended location. It is further ensured that liquid cannot escape between the film and the skin surrounding the area to be treated. Particularly preferable adhesives achieve in a thin add-on of 20 to 35 g/m$^2$ a moisture vapor transmission rate combined with the film of at least 800 g/m$^2$/24 h and preferably of at least 1000 g/m$^2$/24 h (measured to DIN EN 13726).

In accordance with a further developed concept of the present invention, the present invention likewise provides a multilayered wound dressing comprising as a wound contact layer a first layer comprising a water-containing hydrogel matrix, as an absorbent layer a second layer comprising a hydrophilic polymer foam, a backing layer and a distributor layer. More particularly, the absorbent layer is bonded to the wound contact layer. Such a wound dressing very advantageously includes, between the backing layer and the absorbent layer, a distributor layer which consists of a hydrophilic polyurethane foam. The distributor layer provides for distribution of the imbibed wound fluids over the entire area of the wound dressing particularly above the absorbent layer, i.e., the wound fluids are imbibed not just in the z-direction (away from the wound, in the direction of the backing layer), but also in the x-y-direction (over the area of the wound dressing).

In accordance with another further developed concept, the present invention also provides a multilayered wound dressing comprising as a wound contact layer a first layer comprising a water-containing hydrogel matrix, as an absorbent layer a second layer comprising a hydrophilic polymer foam, as a distributor layer a third layer and a backing layer. Any of the abovementioned materials can be used as the backing layer here.

It must be noted here that the herein recited features of the preferred or alternative incarnations of the inventions shall not be restricted to the individual preferences or alternatives. On the contrary, the combination of the embodifications or the combination of the individual features of the alternative forms must similarly count as belonging to an embodification according to the present invention. Similarly, the invention must not be understood as being reduced by the following description of the drawings, where FIG. 1 shows a first inventive wound dressing (view onto the wound contact layer), FIG. 2 shows a second inventive wound dressing in cross section, FIG. 2a shows a detail from the second inventive wound dressing in cross section, FIG. 3 shows a third inventive wound dressing in cross section, and FIG. 3a shows a detail from the third inventive wound dressing in cross section.

FIG. 1 shows a first multilayered wound dressing (10) with the wound contact layer (15) in plan view. The wound dressing (10) consists of a backing layer (not visible here) composed of a water impermeable and moisture vapor permeable polyurethane film uniformly coated with an acrylate adhesive. The backing layer supports an absorbent hydrophilic polyurethane foam layer (not depicted here), onto which a hydrogel matrix has been applied as wound contact layer (15). A multiplicity of circular holes (16) 4.5 mm in diameter have been introduced into the wound contact layer (15) in order that wound exudate may flow through into the absorbent layer. The wound contact layer (15) prevents ingrowth of newly formed cells into the pores of the polyurethane foam. The wound contact layer (15) further exhibits tack in respect of the wound site and the surrounding skin to facilitate application of the secondary dressing. At the same time, the wound contact layer (15) has a pH promotive of wound healing. The holes (16), however, also enable the water in the hydrophilic polyurethane foam to be delivered to the wound. The multilayered wound dressing (10) may also have an adhesive margin, i.e., be fabricated as a so-called island dressing (not depicted here).

FIG. 2 shows a further embodiment of an inventive wound dressing. The wound dressing (20) comprises a backing layer (21) which is congruent to an absorbent layer (23) and is composed of a water impermeable and moisture vapor permeable polyurethane foam. The wound dressing (20) further includes a first water-containing hydrogel matrix (22) between the absorbent layer (23) and the backing layer (21). The water-containing hydrogel matrix serves both to fix the absorbent layer to the backing layer and as an additional water reservoir for the wound dressing. The wound dressing comprises an absorbent layer (23) having a layer thickness of 2.8 mm, a backing layer (21) having a layer thickness of 1.5 mm and a first hydrogel matrix (22) having a layer thickness of 0.8 mm. The absorbent layer (23) is formed from an open-celled hydrophilic polyurethane foam having an average pore size of 208 µm. The polyurethane foam in question comprises a water fraction of at least 10 wt %. On the first side of the polyurethane foam is a second hydrogel matrix applied as a wound contact layer (25). The hydrogel matrix is endowed with cylindrical channels (26) which are circular in cross section (parallel to the wound), and so an improved wound exudate flow from the wound into the absorbent hydrophilic foam can take place. In the course of the production of the wound dressing, the still viscous hydrogel matrix has slightly penetrated into the polyurethane foam, forming between the hydrogel matrix and the hydrophilic polyurethane foam a transition layer (24) which consists of the hydrogel matrix and the hydrophilic polyurethane foam. The transition layer in turn has channels (27) which are filled with polyurethane foam only and which are disposed congruent relative to the channels in the hydrogel matrix. The polyurethane foam comprises a first side having an area of 25 cm², of which the channels (26) altogether occupy an area of about 11 cm².

FIG. 3 shows a third embodiment of an inventive wound dressing. The wound dressing (30) comprises a backing layer (31) composed of a water impermeable and moisture vapor permeable polyurethane film, an absorbent layer (33) composed of an open-celled hydrophilic polyurethane foam having a water content of at least 10 wt % (based on the polyurethane foam) and a wound contact layer (35) composed of a water-containing hydrogel matrix having a water content of about 45 wt % (based on the hydrogel). The backing layer (31) is uniformly laminated onto the hydrophilic polymer foam by means of an acrylate adhesive (32) applied to the polymer film. A water-containing hydrogel matrix (35) comprising a polyurethane-polyurea copolymer has been applied to the absorbent layer's first side, which faces the wound in use. The hydrogel matrix is endowed with conical channels (36) which are circular in cross section (parallel to the wound) and so an improved wound exudate flow from the wound into the absorbent hydrophilic foam can take place (cf. FIG. 3a). In the course of the production of the wound dressing, the still viscous hydrogel matrix has slightly penetrated into the polyurethane foam, forming between the hydrogel matrix and the hydrophilic polyurethane foam a transition layer (34) which consists of the hydrogel matrix and the hydrophilic polyurethane foam. The transition layer in turn has channels (37) which are filled with polyurethane foam only and which are disposed congruent relative to the channels in the hydrogel matrix.

OPERATIVE EXAMPLE

A) TO D) Comparative Examples

A) Producing the Hydrogel (Comparative Example)

The hydrogel is produced using the following aqueous solutions and components (components A, B, C):

Component A

| Propylene glycol USP30 (99.8%) | Hedinger Aug. GmbH; Stuttgart, Germany | 23.24 wt % |
| Aqua purificata | Water treatment plant | 75.41 wt % |
| NaCl, purest, USP | Hedinger Aug. GmbH; Stuttgart, Germany | 1.35 wt % |

Component A is produced by combining the ingredients and stirring until the salt has completely dissolved. Component A is cooled down to 2° C.

Component B

| Jeffamine ED-2003 | Huntsman; Everberg, Belgium | 52.5 wt % |
| Aqua purificata | Water treatment plant | 47.5 wt % |

The aqueous component B is produced by melting the solid Jeffamine at 50° C. and adding the melt to the initially charged water with stirring. Component B is cooled down to room temperature.

Component C

| Aquapol PI-13000-3 | Carpenter; Richmond, USA | 100.0 wt % |

Component C is brought to room temperature.

The ready-made components A, B and C are combined with each other in a ratio of 75.4:14.0:10.6 and homogenized by means of a rotating mixing system to form a homogeneous mixture which is poured ideally without bubbles into the molds provided.

The propylene glycol content of the composition is 17.5 wt %. The ratio for reactive groups of isocyanate to amine groups of diamine in the composition is 1.23.

B1) Polyurethane Foam Used

A hydrophilic polyurethane foam is used (polyurethane foam MCF.03R; from Corpura, -Etten Leur, Netherlands). The dry hydrophilic polyurethane foam has the following characteristics:

a) density: 77.9-83.7 kg/m³ (EN ISO 845)
b) average pore size: 208 μm (determined by microscope on a smaple cross section; the pore size given corresponds to the mean of 5 randomly selected and measured pores per sample)
c) layer thickness: 2.8 mm (thickness measuring instrument with 25 cm² plate, 2 g/cm² load, measured to EN ISO 9073-2)
d) moisture vapor transmission rate: MVTR (upright)=3593 g/m²/24 h (measured to DIN EN 13726-2)
e) absorbency: free absorbency $A_1$=20.5 g/g (measured to DIN EN 13726-1)
f) swell capacity: $\Delta V_0$=89.7%

The swell capacity $\Delta V_0$ of a polyurethane foam describes the volume change experienced by a dry polyurethane foam after it has reached its maximum absorption. To determine swell capacity $\Delta V_0$ the spatial dimensions of a sample piece of the dry polymer foam and the spatial dimensions of this sample piece after complete absorption as per the free absorbency of DIN EN 13726-1 are determined. The thickness (height) is determined using a thickness measuring instrument having a 25 cm² plate adjusted to a loading of 2 g/cm² as per EN ISO 9073-2. The lateral extent (length, width) is determined by means of a vernier without deforming the sample piece. To determine the extent, the particular sample piece is laid tensionlessly onto a smooth surface. The volume change after absorption corresponds to the swell capacity $\Delta V_0$ of the dry polyurethane foam, taking account of all three spatial directions.

|  | Sample 1 | Sample 2 | Sample 3 | Mean | Change/mm (%) |
| --- | --- | --- | --- | --- | --- |
| Length ($l_0$)/mm | 50.0 | 50.0 | 50.0 | 50.0 | — |
| Width ($b_0$)/mm | 50.0 | 50.0 | 50.0 | 50.0 | — |
| Height ($h_0$)/mm | 2.80 | 2.81 | 2.81 | 2.81 | — |
| Length ($l_2$)/mm | 60.2 | 61.9 | 61.3 | 61.1 | 11.1 mm (22.2%) |
| Width ($b_2$)/mm | 61.7 | 63.5 | 62.8 | 62.7 | 12.7 mm (25.4%) |
| Height ($h_2$)/mm | 3.47 | 3.47 | 3.49 | 3.48 | 0.67 mm (23.8%) |

$$\Delta V_0 = \frac{V_2 - V_0}{V_0} \cdot 100\% = \frac{(l_2 \cdot b_2 \cdot h_2) - (l_0 \cdot b_0 \cdot h_0)}{(l_0 \cdot b_0 \cdot h_0)} \cdot 100\% = 89.7\%$$

where:
$V_0$=the volume of the sample piece before absorption (measured under standard conditions (23° C., 50% relative humidity)), and
$V_2$=the volume of the sample piece after complete absorption.

g) Retention value: R=52.8%

The retention value R describes the amount of water which the polyurethane foam can maximally bind in its polyurethane matrix disregarding the water which might be imbibed into the pores. The retention value is determined by die cutting a sample piece of 5 cm×5 cm (stored under standard conditions) out of a hydrophilic polyurethane foam not more than 5 mm in thickness, the weight of which is measured under standard conditions. The sample piece is thereafter subjected to a free absorbency test with water similar to DIN EN 13726-1. The water imbibed by the pores is squeezed out of the sample piece by means of a roller (weight 5000 g, diameter 10 cm, width 5 cm) by the sample being repeatedly placed between fresh paper tissues and rollered. This operation is repeated until there is no visible water absorption in the paper tissues. To determine the retention value R, the water fraction $W_{ww}$, which is present in the polyurethane foam following the absorbing and squeezing out, is measured as per DIN EN 14079 and computed as follows:

|  | Sample 1 | Sample 2 | Mean |
|---|---|---|---|
| Weight dry ($W_{tt}$) | 0.57 g | 0.58 g | 0.58 g |
| Weight after absorption | 11.44 g | 11.75 g | 11.60 g |
| Weight after squeezing out ($W_{gg}$) | 1.22 g | 1.24 g | 1.23 g |

The thickness of the sample pieces measured is 2.80 mm.

$$R = W_{ww}$$
$$= \frac{W_{gg} - W_{tt}}{W_{gg}} \cdot 100\%$$
$$= 52.8\% \text{ (measured to } DIN\ EN\ 14079)$$

where:
$W_{ww}$=weight of water in percent present in the polyurethane foam after absorption and squeezing out
$W_{tt}$=weight of sample piece after drying, and
$W_{gg}$=weight of sample piece after absorption and squeezing out

B2) Conditioning the Polyurethane Foam

The dry hydrophilic polyurethane foam is cut to a size of 20×30 cm and dipped in water for 3 minutes, so that the polyurethane foam reaches its maximum absorption. The polyurethane foam is removed from the water and carefully squeezed out by hand. The polyurethane foam is thereafter repeatedly placed between dry paper tissues and squeezed out by means of a roll (linear pressure 10 N/cm) until no water absorption is visible in the paper tissues. Therefore, the possibility of no water being present in the pores of the foam can be ruled out.

The water-containing polyurethane foam has the following characteristics:

a) Water content: The hydrophilic polyurethane foam has a water fraction $W_w$=52.8 wt % (measured to DIN EN 14079), which corresponds to the retention value R of the dry polyurethane foam.

b) Absorbency: Free absorbency $A_2$=16.2 g/g (measured to DIN EN 13726-1)

c) Swell capacity: $\Delta V_1$=4%

The swell capacity of the water-containing polyurethane foam is determined similarly to the dry polymer foam.

|  | Sample 1 | Sample 2 | Sample 3 | Mean | Change/mm (%) |
|---|---|---|---|---|---|
| Length ($l_1$)/mm | 62.8 | 64.3 | 64.15 | 63.75 | — |
| Width ($b_1$)/mm | 63.4 | 64.45 | 64.3 | 64.05 | — |
| Height ($h_1$)/mm | 3.4 | 3.38 | 3.39 | 3.39 | — |
| Length ($l_2$)/mm | 60.2 | 61.9 | 61.3 | 61.1 | 2.65 mm (4.3%) |
| Width ($b_2$)/mm | 61.7 | 63.5 | 62.8 | 62.7 | 1.35 mm (2.2%) |
| Height ($h_2$)/mm | 3.47 | 3.47 | 3.49 | 3.48 | −0.09 mm (−2.5%) |

$$\Delta V_1 = \frac{V_2 - V_1}{V_1} \cdot 100\% = \frac{(l_2 \cdot b_2 \cdot h_2) - (l_1 \cdot b_1 \cdot h_1)}{(l_1 \cdot b_1 \cdot h_1)} \cdot 100\% = 4\%$$

where:
$V_1$=volume of water-containing sample piece and
$V_2$=volume of sample piece after complete absorption.

C) Further Materials Used

The backing layer used is a water impermeable polyurethane film 60 µm in thickness (from Exopack-Wrexham, United Kingdom). This film is coated with an acrylate-based pressure sensitive adhesive in a layer 30 µm in thickness. The film has a moisture vapor transmission rate MVTR (upright) of 1100 g/m²/24 h (DIN EN 13726-1).

D) Producing the Wound Dressings

The wound dressings (specimens) are fabricated by hand in accordance with the following sequence:

1. The polyurethane foam is preconditioned as per B) and provided.
2. To produce a hydrogel matrix having channels a PTFE mold having a dimpled texture is provided. The dimples of the dimpled texture are cone-shaped and have an average diameter of 1.38 mm (base 1.56 mm, tip 1.2 mm). The dimples are 1.35 mm high and are spaced 5 mm apart in a rectangular pattern.
3. The hydrogel is produced as per A) and provided, although the hydrogel has to be further processed without delay after the commixing and homogenizing. To this end, the hydrogel is poured ideally without bubbles into the provided molds to form the hydrogel matrix.

4. The gel is distributed with a PTFE blade such that the gel layer has the height of the dimples (1.35 mm). Excess gel is removed from the mold.
5. After about 3 minutes, the preconditioned polyurethane foam is laid onto the gel surface. A pressure of 200 N/m² is applied to the foam to press and hold it down.
6. After about 7 minutes more, the gel has become bonded to the foam, so that the laminate of water-containing polyurethane foam and water-containing hydrogel matrix can be removed from the mold. A transition layer consisting of water-containing hydrogel matrix and water-containing polyurethane foam has formed in a thickness of 0.3 mm.
7. The laminate is placed with the hydrogel side face down onto the prepared release film (the siliconized side faces the gel), so that the side facing the wound is protected.
8. The assembly is covered on the foam side with a self-adhesive polyurethane film (cf. D), and the polyurethane film is firmly pressed in place using a pressure of 200 N/m².
9. Wound dressings having an edge length of 10×10 cm are die cut out of the multi-ply material assembly.

The wound dressing thus produced has the construction described using FIG. 3, although FIG. 3 does not show a release liner. The wound dressing thus consists of a laminate composed of a flexible water-containing hydrogel matrix as wound contact layer, which contains 63.5 wt % of water (based on the hydrogel matrix), and an absorbent layer composed of an open-celled hydrophilic polyurethane foam having a water fraction of 52.8 wt % (based on the polyurethane foam).

The wound dressing further has the following characteristics:
a) Basis weight: 1550 g/m² (measured to DIN EN 29073-1)
b) Absorbency: free absorbency $A_1$=56 g/100 cm² (measured to DIN EN 13726-1)
c) Water content in total:

$$W_w = \frac{W_g - W_t}{W_g} \cdot 100\% = 58.8 \text{ wt \%}$$

d) Swell capacity: $\Delta V$=10% (measured as per method described above)

The present wound dressing thus has a high water content, a high absorbency and a low swell. The wound dressing is thus optimally suitable for use in wound healing phases 2 and 3 (granulation phase and epithelization phase).

The wound dressing does not adhere to skin. The tack of the wound dressing is rated 1. The wound dressing has to be held down by hand on the wound site when the bandage is applied, until it is secured, for example by a retaining bandage or an adhesive plaster. It can therefore be advantageous for the wound dressing to have an adhesive border, i.e., for it to be configured as a so-called island dressing.

E) Producing a Hydrogel

The procedure described above under A) is repeated to produce further hydrogel matrices having the following compositions other than A). All particulars in wt % are based on the composition.

| Experiment | Isocyanate[1] | Diamine[2] | Polyurea[3] | NCO/NH2[4] | Propylene glycol | Water | NaCl |
|---|---|---|---|---|---|---|---|
| 1.10 | 10.5 | 6.5 | 17.0 | 1.30 | 60.0 | 22.1 | 0.9 |
| 2.1.5 | 9.27 | 5.73 | 15.0 | 1.30 | 40.0 | 44.1 | 0.9 |
| 2.1.11 | 10.3 | 7.2 | 17.5 | 1.15 | 40.0 | 41.5 | 0.9 |

[1]Aquapol PI-13000-3 isocyanate prepolymer, proportion of reactive groups (NCO) 3.223%
[2]Jeffamine ED-2003 diamine (molecular weight 2000), amine content 0.9554 mol/g
[3]sum total of isocyanate and diamine
[4]ratio for reactive groups of isocyanate to amine groups of diamine F) Producing a Multilayered Wound Dressing An inventive wound dressing is produced using a hydrogel composition as described above under E) as the first layer. A polyurethane foam as described above under B1) is further used as the second layer. The wound dressing further comprises the backing layer described under C). The hydrogel has a thickness of 1.0 mm in each case after pouring. The thickness of the hydrogel is only 0.8 mm after the hydrogel has been laminated with the polyurethane foam. The laminating has the effect of forming, between the hydrogel and the polyurethane foam, a further, hybrid layer ("transition layer") which consists of water-containing polyurethane foam and water-containing hydrogel matrix. The transition layer is the result of the incompletely cured gel partially migrating into the openings in the foam. The further, hybrid layer, which is about 0.3 mm in thickness, is only formed in those places on the polyurethane foam layer which are in contact with the hydrogel. No further, hybrid layer is formed in the region of the openings introduced into the hydrogel. The formation of a further, hybrid layer between the first layer and the second layer is desirable because the further, hybrid layer enhances the laminate stability.

The wound dressings (specimens) are fabricated by hand in accordance with the following sequence:
1. To produce a hydrogel matrix having channels a PTFE mold (Teflon) having a dimpled texture is provided. The dimples of the dimpled texture are 1.0 mm high and cone-shaped. The middle diameter of the dimples is 4.5 mm (base 5.1 mm, tip 3.9 mm). The midpoints of the dimples in any one row are separated from each other by 6.5 mm, so that the hydrogel forms gel struts 2 mm in width after pouring. Row separation at 5.63 mm is such that the midpoints of three holes form an equilateral triangle. The rows are accordingly in an arrangement where they are offset relative to each other. The arrangement ensures a homogeneous distribution for the open area of the hydrogel. The area accounted for by the openings in the hydrogel amounts to about 43.5% on the wound side.
2. The hydrogel composition is produced as per E), although the hydrogel has to be immediately further processed after the commixing and homogenizing. To this end, the hydrogel is poured, ideally without bubbles, into the mold mentioned under 1) to form the hydrogel matrix.

3. The gel is distributed with a PTFE squeegee such that the gel layer has the height of the dimples, i.e., about 1 mm. Excess gel is removed from the mold.
4. After about 3 minutes, the polyurethane foam is laid onto the gel surface before the hydrogel has fully cured. A pressure of 200 N/m² is applied to the foam to hold it down and keep it in place.
5. After about 7 minutes, the gel has become bonded to the foam, so that the laminate of water-containing polyurethane foam and water-containing hydrogel matrix can be removed from the mold. A transition layer consisting of water-containing hydrogel matrix and water-containing polyurethane foam has formed in a thickness of about 0.3 mm at the area of contact between the hydrogel and the polyurethane foam.
6. The laminate is laid with the hydrogel side face down onto the prepared siliconized release film (the siliconized side faces the gel). The release film serves to protect the wound contact layer.
7. The assembly is covered on the polyurethane foam side with a self-adhesive polyurethane film (cf. C), and the polyurethane film is firmly held down in place for at least 10 seconds under a pressure of 200 N/m².
8. Wound dressings having an edge length of 10×10 cm are die cut out of the multi-ply assembly.

In contradistinction to the procedure described under D), the polyurethane foam was not preconditioned, i.e., step 1 of D) was omitted.

The wound dressing thus produced has the construction described using FIG. 3, although FIG. 3 does not show a release liner.

G) Methods of Measurement

Absorptive capacity in respect of demineralized water is determined in line with EN13726-1. The measurement takes place at 37° C. Sample pieces 2.5×2.5 cm in size are cut out of the middle of the hydrogel layer. Any covering film is peeled off and removed. The samples are weighed into a glass beaker. Demineralized water is then added in 40 times the amount. The glass beaker is covered with a watch glass. After 48 h the samples are reweighed. Water imbibition is computed in g of water per g of gel piece (g/g).

The pH of a wound dressing is determined in connection with the present invention by laying the laminate of hydrogel and polyurethane foam (without backing layer and release film) into water and measuring the pH of the solution. The measurement is carried out at room temperature (20° C.). Sample pieces 2.5×2.5 cm in size are cut out of the middle of the hydrogel layer. Any covering film is peeled off and removed. The samples are weighed into a glass beaker. Demineralized water is then added in an amount of 12.5 ml. The glass beaker is covered with a watch glass. After a period of 24 h the sample is removed from the solution. A pH electrode is then dipped into the solution temperature-controlled to 20° C. The pH is read off as soon as the displayed numerical value remains stable.

The tack of the wound dressing to intact skin was estimated. Commercially available products were put into 5 categories by one person. A tack of 1 on the scale indicates that the wound dressing does not adhere to healthy skin, while a tack of 5 indicates a very high level of tack. It was assessed on the basis of the subjective impression of one person by comparison with the tack of the prepared wound dressings as perceived between the index finger and the gel.

H) Properties of Wound Dressings

|  | Tack | pH | Absorbency |
|---|---|---|---|
| Wound dressing[1] with hydrogel from exp. 1.10 | 5 | 8.83 | 8.63 g/g |
| Wound dressing[1] with hydrogel from exp. 2.1.5 | 4 | 7.44 | 8.55 g/g |
| Wound dressing[1] with hydrogel from exp. 2.1.11 | 5 | 8.18 | 9.98 g/g |
| Wound dressing[2] from exp. A to C) | 1 | not measured | |

[1]hydrogel thickness 0.8 mm; polyurethane foam thickness 2.8 mm
[2]hydrogel thickness 1.35 mm; polyurethane foam thickness 2.8 mm
[3]amount of demineralized water absorbed after 48 h based on own weight (g/g)

The wound dressings have a high water content, a high absorbency and a low swell.

The wound dressing with the hydrogel from experiment 1.10 has an undesirably high pH of 8.83, which is not promotive of wound healing. The wound dressing further has a tack of 5, i.e., the wound dressing adheres very firmly to skin, but is not entirely painless to remove. The very high tack of 5 could damage the sensitive wound edges in particular when changing the bandage.

The wound dressing with the hydrogel from experiment 2.1.5 has a very advantageous pH of 7.44, which augments wound healing. The wound dressing further has a tack of 4, i.e., the wound dressing adheres firmly to skin and is easy to remove. The tack is in the desired range.

The wound dressing with the hydrogel from experiment 2.1.11 has an undesirably high pH of 8.18. The wound dressing further has a tack of 5, i.e., the wound dressing adheres very firmly to skin, but is not entirely painless to remove. The very high tack of 5 could damage the sensitive wound edges in particular when changing the bandage.

The wound dressing produced according to A) to C) does not adhere to skin (tack is 1).

What is claimed is:
1. A multilayered wound dressing comprising:
   a) a first layer as a wound contact layer comprising a water-containing hydrogel matrix, and
   b) at least one second absorbent layer which is a hydrophilic polyurethane foam,
   characterized in that the hydrogel matrix comprises from 37 to 43 wt % of propylene glycol, altogether from 12 to 16.5 wt % of a prepolymer having isophorone diisocyanate end groups and of a diamine based on polyethylene oxide and from 0 to 5 wt % of an inorganic chloride, balance water, wherein the ratio for reactive groups of isocyanate to amine groups of diamine shall be in the range from 1.25 to 1.35, wherein the hydrogel matrix has a pH of less than 8; and, wherein the wound dressing further comprises a water impermeable and moisture vapor permeable polymer film, or a water impermeable and moisture vapor permeable polymer foam, as a backing layer wherein the hydrophilic polyurethane foam has a water content of at least 35 wt % of water and at most 65 wt % of water.
2. The wound dressing according to claim 1, wherein the hydrogel matrix comprises from 8 to 10.5 wt % of a prepolymer having isophorone diisocyanate end groups and from 4 to 6 wt % of a diamine based on polyethylene oxide.
3. The wound dressing according to claim 1, wherein the hydrogel matrix comprises from 39 to 41 wt % of propylene glycol and altogether from 14 to 16 wt % of a prepolymer having isophorone diisocyanate end groups and of a diamine based on polyethylene oxide.

4. The wound dressing according to claim 1, wherein the hydrogel matrix comprises 40 wt % of propylene glycol, 8.5 wt % of a prepolymer having isophorone diisocyanate end groups and 6.5 wt % of a diamine based on polyethylene oxide.

5. The wound dressing according to claim 1, wherein the water forms a homogeneous distribution in the polyurethane foam.

6. The wound dressing according to claim 1, wherein the hydrophilic polyurethane foam has an ISO1798-M1 elongation at break in the range from 50 to 105 kPa when in a dry state.

7. The wound dressing according to claim 1, wherein the hydrophilic polyurethane foam has a thickness of from 2.0 to 5.5 mm.

8. The wound dressing according claim 1, wherein the wound contact layer has a multiplicity of holes, channels or openings passing completely through the wound contact layer to allow liquid to pass from the outside through the wound contact layer to the second absorbent layer.

9. The wound dressing according to claim 8, wherein the holes, channels or openings are in a regular pattern.

10. The wound dressing according to claim 8, wherein the holes, channels or openings occupy from 15% to 70% of the area of the wound contact layer.

11. The wound dressing according to claim 8, wherein the wound contact layer has holes, channels or openings each of from 3 to 5 mm in diameter.

12. The wound dressing according to claim 1, wherein the wound contact layer is from 0.6 to 1.0 mm in thickness.

13. The wound dressing according to claim 1, wherein the wound contact layer further comprises a polymer film, a hydrocolloid matrix, a polymer mesh, a nonwoven material or an adhesive.

14. A process for producing a multilayered wound dressing according to claim 1, said process comprising the steps of:
  a) providing a hydrophilic polyurethane foam, wherein the polyurethane foam has a water content of at least 35 wt % of water and at most 65 wt % of water,
  b) laminating the water-containing polyurethane foam produced under a) onto a hydrogel matrix, wherein the hydrogel matrix comprises from 37 to 43 wt % of propylene glycol, altogether from 12 to 16.5 wt % of a prepolymer having isophorone diisocyanate end groups and of a diamine based on polyethylene oxide and from 0 to 5 wt % of an inorganic chloride, and balance water, such that the ratio for reactive groups of isocyanate to amine groups of diamine is in the range of from 1.25 to 1.35.

* * * * *